(12) United States Patent
Nakamura et al.

(10) Patent No.: US 8,134,019 B2
(45) Date of Patent: Mar. 13, 2012

(54) PROCESS FOR PRODUCING FULLERENE DERIVATIVE

(75) Inventors: Eiichi Nakamura, Tokyo (JP); Yutaka Matsuo, Tokyo (JP); Akihiko Iwashita, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 448 days.

(21) Appl. No.: 12/514,782

(22) PCT Filed: Nov. 6, 2007

(86) PCT No.: PCT/JP2007/071868
§ 371 (c)(1),
(2), (4) Date: Jun. 9, 2009

(87) PCT Pub. No.: WO2008/059771
PCT Pub. Date: May 22, 2008

(65) Prior Publication Data
US 2010/0048934 A1    Feb. 25, 2010

(30) Foreign Application Priority Data

Nov. 14, 2006  (JP) ................................. 2006-308357

(51) Int. Cl.
C07C 2/64      (2006.01)
C07C 13/64     (2006.01)
C07C 41/30     (2006.01)
C07C 43/21     (2006.01)
C07F 7/08      (2006.01)
C07F 7/18      (2006.01)

(52) U.S. Cl. ......... 556/466; 556/431; 556/432; 556/465

(58) Field of Classification Search ........................ None
See application file for complete search history.

(56) References Cited

U.S. PATENT DOCUMENTS

2003/0139617 A1    7/2003    Nakamura et al.

FOREIGN PATENT DOCUMENTS

| JP | 7-089972    | 4/1995 |
| JP | 10-167994   | 6/1998 |
| JP | 11-255509   | 9/1999 |
| JP | 2003-212881 | 7/2003 |
| JP | 2005-232165 | 9/2005 |

OTHER PUBLICATIONS

Translation of JP-2005-232165; published 2005.*
Martin et al., "$C_{60}$-based electroactive organofullerenes", Chem. Rev., 98: 2527-2547 (1998).
Sawamura et al., "Pentaorgano[60]fullerene $R_5C_{60}^-$ A water soluble hydrocarbon anion", Chem. Lett., 1098-1099 (2000).
Sawamura et al., "Stepwise synthesis of fullerene cyclopentadienide $R_5C_{60}^-$ and indenide $R_3C_{60}^-$. An approach to fully unsymmetrically substituted derivatives", Org. Lett., 2(13): 1919-1921 (2000).
Sawamura et al., "The first pentahaptofullerene metal complexes", J. Am. Chem. Soc., 118: 12850-12851 (1996).

* cited by examiner

*Primary Examiner* — Daniel Sullivan
*Assistant Examiner* — Yevegeny Valenrod
(74) *Attorney, Agent, or Firm* — Morgan, Lewis & Bockius LLP

(57) ABSTRACT

The present invention provides a method for producing a fullerene derivative, comprising the organic group addition step B in which an organic group is further added by reacting at least a basic compound and a halogen compound with a fullerene derivative, which is obtained by addition of a hydrogen atom and an organic group in the organic group addition step A, in which an organic group is added by reacting at least a Grignard reagent and a polar substance with a fullerene or fullerene derivative.

21 Claims, No Drawings

PROCESS FOR PRODUCING FULLERENE DERIVATIVE

This application is a U.S. National Phase Application of International Application Number PCT/JP2007/071868 filed Nov. 6, 2007, which claims the benefit of Japanese Patent Application No. 2006-308357, filed Nov. 14, 2006, each of which is incorporated by reference in its entirety.

TECHNICAL FIELD

The present invention relates to a method for producing a fullerene derivative. Specifically, the present invention relates to a method for producing a fullerene derivative comprising the step of adding an organic group to a fullerene or fullerene derivative.

BACKGROUND ART

Since the method for synthesizing a carbon cluster (hereinafter also referred to as "fullerene"), in which carbon atoms are arranged to form a spherical shape or a rugby ball shape, was established, fullerene has been energetically studied. As a result many fullerene derivatives have been synthesized.

With respect to specific examples of such fullerene derivatives, methods for synthesizing a fullerene derivative, in which 5 organic groups bind to a fullerene skeleton (hereinafter also just referred to as "penta(organo)fullerene derivative"), have been reported (e.g., Japanese Laid-Open Patent Publication No. Hei 10-167994 (Patent document 1); Japanese Laid-Open Patent Publication No. Hei 11-255509 (Patent document 2); J. Am. Chem. Soc., 118, 12850 (1996) Son-patent document 1); Org. Lett., 2, 1919 (2000) (Non-patent document 2); and Chem. Lett., 1098 (2000) (Non-patent document 3)).

As a method for producing a penta(organo)fullerene derivative, for example, it is known that, by reacting an organocopper reagent prepared using a phenyl Grignard reagent and $CuBr \cdot S(CH_3)_2$ with fullerene $C_{60}$, a phenylated fullerene derivative, in which phenyl groups constituting the phenyl Grignard reagent are regioselectively added to surround one 5-membered ring of fullerene $C_{60}$ ($C_{60}Ph_5H$), can be quantitatively obtained (e.g., Japanese Laid-Open Patent Publication No. 10-167994 (Patent document 1)).

The method for producing a fullerene derivative using the phenyl Grignard reagent and the organocopper reagent is extremely effective for production of a hexa(organo)fullerene derivative, a hepta(organo)fullerene derivative, a deca(organo)fullerene derivative or the like, realizing a high yield of a product of interest. However, there is a problem that, when synthesizing a fullerene derivative in which the number of substituents added is small (e.g., a mono(organo)fullerene derivative, a di(organo)fullerene derivative, a tri(organo)fullerene derivative, and a tetra(organo)fullerene derivative) using this method, the yield thereof is low.

DISCLOSURE OF THE INVENTION

Under the above-described circumstances, for example, a method for producing a fullerene derivative in which the number of substituents added is small (e.g., a mono(organo) fullerene derivative, a di(organo)fullerene derivative, a tri (organo)fullerene derivative, and a tetra(organo)fullerene derivative) in good yield is desired. The present inventors found a method for producing a fullerene derivative comprising the step of regioselectively adding an organic group to a fullerene or fullerene derivative by reacting at least a Grignard reagent and a polar substance with the fullerene (derivative) (organic group addition step A). Moreover, the present inventors found a method for producing a fullerene derivative comprising the step of further adding an organic group by reacting at least a basic compound and a halogen compound after the organic group addition step A (organic group addition step B). The present inventors achieved the present invention based on these findings.

The present invention provides a method for producing a fullerene derivative, etc. as follows.

[1] A method for producing a fullerene derivative comprising the organic group addition step A for adding an organic group by reacting at least a Grignard reagent and a polar substance with a fullerene or fullerene derivative, in which the polar substance is used in an amount of 3 to 100 equivalents of the fullerene or fullerene derivative to which the organic group is added. That is, in the method in item [1], the polar substance in an amount of 3 to 100 equivalents of the fullerene or fullerene derivative is put in a reaction system in which a reaction step for addition of the organic group is carried out.

[2] The method for producing a fullerene derivative according to item [1], in which the fullerene or fullerene derivative to which the organic group is added in the organic group addition step A is a fullerene or fullerene derivative represented by the following formula (1):

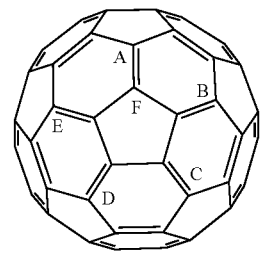

(1)

wherein: organic groups have been each independently added to 0 to 4 carbons among 5 carbons positioned at A to E; and a hydrogen atom or $C_1$-$C_{30}$ hydrocarbon group has been added to a carbon positioned at F, or nothing has been added thereto.

[3] The method for producing a fullerene derivative according to item [2], wherein in the organic group addition step A, the organic group is added to at least one of the carbons positioned at A to E in the fullerene or fullerene derivative represented by formula (1) to which the organic group has not been added.

[4] The method for producing a fullerene derivative according to any one of items [1] to [3], wherein the organic group for addition in the organic group addition step A is one or more substances selected from the group consisting of a hydrogen atom, a substituted or unsubstituted $C_1$-$C_{30}$ hydrocarbon group, a substituted or unsubstituted $C_1$-$C_{30}$ alkoxy group, a substituted or unsubstituted $C_6$-$C_{30}$ aryloxy group, a substituted or unsubstituted amino group, a substituted or unsubstituted silyl group, a substituted or unsubstituted alkylthio group (—$SY^1$: in the formula, $Y^1$ is a substituted or unsubstituted $C_1$-$C_{20}$ alkyl group), a substituted or unsubstituted arylthio group (—$SY^2$: in the formula, $Y^2$ is a substituted or unsubstituted $C_6$-$C_{18}$ aryl group), a substituted or unsubstituted alkylsulfonyl group (—$SO_2Y^3$: in the formula, $Y^3$ is a substituted or unsubstituted $C_1$-$C_{20}$ alkyl group), and a substituted or unsubstituted arylsulfonyl group (—SO$_2$Y$^4$: in the formula, Y$^4$ is a substituted or unsubstituted C$_6$-C$_{18}$ aryl group).

[5] The method for producing a fullerene derivative according to any one of items [1] to [3], wherein the organic group for addition in the organic group addition step A is a group represented by the following formula (2):

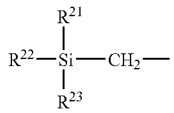
(2)

wherein R$^{21}$ to R$^{23}$ are each independently a hydrogen atom, a substituted or unsubstituted C$_1$-C$_{30}$ hydrocarbon group, a substituted or unsubstituted C$_1$-C$_{30}$ alkoxy group, a substituted or unsubstituted C$_6$-C$_{30}$ aryloxy group, a substituted or unsubstituted amino group, a substituted or unsubstituted silyl group, a substituted or unsubstituted alkylthio group (—SY$^1$: in the formula, Y$^1$ is a substituted or unsubstituted C$_1$-C$_{20}$ alkyl group), a substituted or unsubstituted arylthio group (—SY$^2$: in the formula, Y$^2$ is a substituted or unsubstituted C$_6$-C$_{18}$ aryl group), a substituted or unsubstituted alkylsulfonyl group (—SO$_2$Y$^3$: in the formula, Y$^3$ is a substituted or unsubstituted C$_1$-C$_{20}$ alkyl group), or a substituted or unsubstituted arylsulfonyl group (—SO$_2$Y$^4$: in the formula, Y$^4$ is a substituted or unsubstituted C$_6$-C$_{18}$ aryl group).

[6] The method for producing a fullerene derivative according to item [5], wherein R$^{21}$ to R$^{23}$ are each independently a C$_1$-C$_{20}$ alkyl group,

[7] The method for producing a fullerene derivative according to any one of items [1] to [6], wherein the Grignard reagent is represented by the following formula (3):

R$^3$MgX (3)

wherein: R$^3$ represents an organic group; and X represents Cl, Br or I.

[8] The method for producing a fullerene derivative according to item [7], wherein R$^3$ in formula (3) is a substituted or unsubstituted C$_1$-C$_{30}$ hydrocarbon group, a substituted or unsubstituted C$_1$-C$_{30}$ alkoxy group, a substituted or unsubstituted C$_6$-C$_{30}$ aryloxy group, a substituted or unsubstituted amino group, a substituted or unsubstituted silyl group, a substituted or unsubstituted alkylthio group (—SY$^1$: in the formula, Y$^1$ is a substituted or unsubstituted C$_1$-C$_{20}$ alkyl group), a substituted or unsubstituted arylthio group (—SY$^2$: in the formula, Y$^2$ is a substituted or unsubstituted C$_6$-C$_{18}$ aryl group), a substituted or unsubstituted alkylsulfonyl group (—SO$_2$Y$^3$: in the formula, Y$^3$ is a substituted or unsubstituted C$_1$-C$_{20}$ alkyl group), or a substituted or unsubstituted arylsulfonyl group (—SO$_2$Y$^4$: in the formula, Y$^4$ is a substituted or unsubstituted C$_6$-C$_{18}$ aryl group).

[9] The method for producing a fullerene derivative according to item [8], wherein R$^3$ is a C$_1$-C$_{20}$ alkyl group.

[10] The method for producing a fullerene derivative according to any one of items [1] to [9], wherein the Grignard reagent is used in an amount of 1 to 20 equivalents of the fullerene or fullerene derivative to which the organic group is added in the organic group addition step A. That is, in the method in item [10], the Grignard reagent in an amount of 1 to 20 equivalents of the fullerene or fullerene derivative is put in the reaction system in which the reaction step for addition of the organic group is carried out.

[11] The method for producing a fullerene derivative according to any one of items [1] to [10], wherein the donor number of the polar substance is 25 or more.

[12] The method for producing a fullerene derivative according to any one of items [1] to [10], wherein the polar substance is N,N-dimethylformamide, dimethyl sulfoxide or pyridine.

[13] The method for producing a fullerene derivative according to any one of items [1] to [12], wherein the fullerene derivative to which the organic group has been added in the organic group addition step A is a fullerene derivative represented by the following formula (1A):

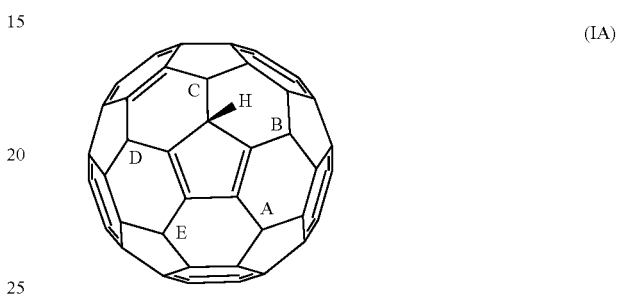
(1A)

wherein: organic groups have been each independently added to 1 to 5 carbons among 5 carbons positioned at A to E.

[14] The method for producing a fullerene derivative according to item [13], wherein in formula (1A), the organic groups added to the carbons positioned at A to ED are each independently a hydrogen atom, a substituted or unsubstituted C$_1$-C$_{30}$ hydrocarbon group, a substituted or unsubstituted C$_1$-C$_{30}$ alkoxy group, a substituted or unsubstituted C$_6$-C$_{30}$ aryloxy group, a substituted or unsubstituted amino group, a substituted or unsubstituted silyl group, a substituted or unsubstituted alkylthio group (—SY$^1$: in the formula, Y$^1$ is a substituted or unsubstituted C$_1$-C$_{20}$ alkyl group), a substituted or unsubstituted arylthio group (—SY$^2$: in the formula, Y$^2$ is a substituted or unsubstituted C$_6$-C$_{18}$ aryl group), a substituted or unsubstituted alkylsulfonyl group (—SO$_2$Y$^3$: in the formula, Y$^3$ is a substituted or unsubstituted C$_1$-C$_{20}$ alkyl group), or a substituted or unsubstituted arylsulfonyl group (—SO$_2$Y$^4$: in the formula, Y$^4$ is a substituted or unsubstituted C$_6$-C$_{18}$ aryl group).

[15] The method for producing a fullerene derivative according to any one of items [1] to [14], which comprises the organic group addition step B for further adding an organic group by reacting at least a basic compound and a halogen compound with the fullerene derivative obtained by addition of a hydrogen atom and an organic group in the organic group addition step A.

[16] The method for producing a fullerene derivative according to item [15], wherein the basic compound to be used in the organic group addition step B comprises one or more substances selected from the group consisting of a metal hydride, a metal alkoxide, an alkali metal reagent, an alkali metal and an organic alkali.

[17] The method for producing a fullerene derivative according to item [15], wherein the basic compound to be used in the organic group addition step B is alkoxide comprising K or Na.

[18] The method for producing a fullerene derivative according to item [15], wherein the basic compound to be used in the organic group addition step B is t-BuOK or t-BuONa.

[19] The method for producing a fullerene derivative according to any one of items [15] to [18], wherein the halogen compound to be used in the organic group addition step B is represented by the following formula (4):

$$R^4X \qquad (4)$$

wherein: $R^4$ represents an organic group; and X represents a halogen atom.

[20] The method for producing a fullerene derivative according to item [19], wherein in formula (4): $R^4$ is a hydrogen atom, a substituted or unsubstituted $C_1$-$C_{30}$ hydrocarbon group, a substituted or unsubstituted $C_1$-$C_{30}$ alkoxy group, a substituted or unsubstituted $C_6$-$C_{30}$ aryloxy group, a substituted or unsubstituted amino group, a substituted or unsubstituted silyl group, a substituted or unsubstituted alkylthio group (—$SY^1$: in the formula, $Y^1$ is a substituted or unsubstituted $C_1$-$C_{20}$ alkyl group), a substituted or unsubstituted arylthio group (—$SY^2$: in the formula, $Y^2$ is a substituted or unsubstituted $C_6$-$C_{18}$ aryl group), a substituted or unsubstituted alkylsulfonyl group (—$SO_2Y^3$: in the formula, $Y^3$ is a substituted or unsubstituted $C_1$-$C_{20}$ alkyl group), or a substituted or unsubstituted arylsulfonyl group (—$SO_2Y^4$: in the formula, $Y^4$ is a substituted or unsubstituted $C_6$-$C_{18}$ aryl group); and X is Cl, Br or I.

As used herein, "fullerene" is a general term for carbon clusters which are formed by arranging carbon atoms in a spherical shape or a rugby ball shape (see Gendai-Kagaku, June 2000, page 46; and Chemical Reviews, 98, 2527 (1998)). Examples thereof include fullerene $C_{60}$ (so-called buckminsterfullerene), fullerene $C_{70}$, fullerene $C_{76}$, fullerene $C_{78}$, fullerene $C_{82}$, fullerene $C_{84}$, fullerene $C_{90}$, fullerene $C_{94}$, and fullerene $C_{96}$.

When the method for producing a fullerene derivative according to the preferred embodiment of the present invention is used, a fullerene derivative in which the number of groups added is small (e.g., a mono(organo)fullerene derivative, a di(organo)fullerene derivative, a tri(organo)fullerene derivative, and a tetra(organo)fullerene derivative) can be produced in good yield.

When the method for producing a fullerene derivative according to the preferred embodiment of the present invention is used, specific organic groups can be added to the fullerene or fullerene derivative in a stepwise manner, and moreover, the aforementioned organic groups can be regioselectively added thereto.

Furthermore, when the method for producing a fullerene derivative according to the preferred embodiment of the present invention is used, a fullerene derivative in which specific organic groups are added to specific positions of the fullerene derivative can be selectively produced.

BEST MODE FOR CARRYING OUT THE INVENTION

I. Organic Group Addition Step A of the Present Invention

The organic group addition step A of the present invention is a step of adding an organic group by reacting at least a Grignard reagent and a polar substance with a fullerene or fullerene derivative.

1. Fullerene or Fullerene Derivative to which Organic Group is Added in the Organic Group Addition Step A 1.1. Fullerene to which Organic Group is Added in the Organic Group Addition Step A A fullerene to which the organic group is added in the organic group addition step A of the present invention is not particularly limited, and examples thereof include fullerene $C_{60}$ (so-called buckminsterfullerene), fullerene $C_{70}$, fullerene $C_{76}$, fullerene $C_{78}$, fullerene $C_{82}$, fullerene $C_{84}$, fullerene $C_{90}$, fullerene $C_{94}$, and fullerene $C_{96}$. Among them, a fullerene in which nothing has been added to the carbons at the positions A to F in the above-described formula (1) is particularly preferred.

There is no specific limitation on the method for producing a fullerene, and a fullerene produced according to a publicly-known method can be used as a starting material for the production method of the present invention. One type of fullerene or a mixture of two or more types of fullerenes can be suitably used.

1.2. Fullerene Derivative to which Organic Group is Added in the Organic Group Addition Step A A fullerene derivative to which the organic group is added in the organic group addition step A of the present invention is a fullerene derivative in which the organic group has been added to a fullerene. Further, a fullerene, which is the basic skeleton of the fullerene derivative, is the same as the fullerene as the starting material in the production method of the present invention.

The fullerene derivative to which the organic group is added in the organic group addition step A is preferably a mono(organo)fullerene derivative in which one organic group has been added or a di(organo)fullerene derivative in which two organic groups have been added, but is not limited thereto.

As the fullerene derivative to which the organic group is added in the organic group addition step A, a fullerene derivative in which a hydrogen atom or organic group has been added to one or more carbons among those positioned at A to F in the above-described formula (1) is preferred.

Regarding the fullerene derivative to which the organic group is added in the organic group addition step A of the present invention, the organic group to be added to the fullerene skeleton is not particularly limited, and examples thereof include a hydrogen atom, a substituted or unsubstituted $C_1$-$C_{30}$ hydrocarbon group, a substituted or unsubstituted $C_1$-$C_{20}$ alkoxy group, a substituted or unsubstituted $C_6$-$C_{20}$ aryloxy group, a substituted or unsubstituted amino group, a substituted or unsubstituted silyl group, a substituted or unsubstituted alkylthio group (—$SY^1$: in the formula, $Y^1$ is a substituted or unsubstituted $C_1$-$C_{20}$ alkyl group), a substituted or unsubstituted arylthio group (—$SY^2$: in the formula, $Y^2$ is a substituted or unsubstituted $C_6$-$C_{18}$ aryl group), a substituted or unsubstituted alkylsulfonyl group (—$SO_2Y^3$: n the formula, $Y^3$ is a substituted or unsubstituted $C_1$-$C_{20}$ alkyl group), and a substituted or unsubstituted arylsulfonyl group (—$SO_2Y^4$: in the formula, $Y^4$ is a substituted or unsubstituted $C_6$-$C_{18}$ aryl group).

In the present specification, the hydrocarbon group of the "$C_1$-$C_{30}$ hydrocarbon group" may be a saturated or unsaturated acyclic group or a saturated or unsaturated cyclic group. When the $C_1$-$C_{30}$ hydrocarbon group is acyclic, it may be linear or branched. The "$C_1$-$C_{30}$ hydrocarbon group" includes $C_1$-$C_{30}$ alkyl group, $C_2$-$C_{30}$ alkenyl group, $C_2$-$C_{30}$ alkynyl group, $C_4$-$C_{30}$ alkyldienyl group, $C_6$-$C_{28}$ aryl group, $C_7$-$C_{30}$ alkylaryl group, $C_7$-$C_{30}$ arylalkyl group, $C_4$-$C_{30}$ cycloalkyl group, $C_4$-$C_{30}$ cycloalkenyl group, and ($C_3$-$C_{15}$ cycloalkyl) $C_1$-$C_{15}$ alkyl group.

In the present specification, the "$C_1$-$C_{30}$ alkyl group" is preferably $C_1$-$C_{20}$ alkyl group, and more preferably $C_1$-$C_{10}$ alkyl group. Examples of alkyl groups include, but are not limited to, methyl, ethyl, propyl, isopropyl, n-butyl, sec-butyl, tert-butyl, pentyl, hexyl, and dodecanyl.

In the present specification, the "$C_2$-$C_{30}$ alkenyl group" is preferably $C_2$-$C_{20}$ alkenyl group, and more preferably $C_2$-$C_{10}$ alkenyl group. Examples of alkenyl groups include, but are not limited to, vinyl, allyl, propenyl, isopropenyl, 2-methyl-1-propenyl, 2-methylallyl, and 2-butenyl.

In the present specification, the "$C_2$-$C_{30}$ alkynyl group" is preferably $C_2$-$C_{20}$ alkynyl group, and more preferably $C_2$-$C_{10}$ alkynyl group. Examples of alkynyl groups include, but are not limited to, ethynyl, propynyl, and butynyl.

In the present specification, the "$C_4$-$C_{30}$ alkyldienyl group" is preferably $C_4$-$C_{20}$ alkyldienyl group, and more preferably $C_4$-$C_{10}$ alkyldienyl group. Examples of alkyldienyl groups include, but are not limited to, 1,3-butadienyl.

In the present specification, the "$C_6$-$C_{28}$ aryl group" is preferably $C_6$-$C_{10}$ aryl group. Examples of aryl groups include, but are not limited to, phenyl, 1-naphthyl, 2-naphthyl, indenyl, biphenylyl, anthryl, and phenanthryl.

In the present specification, the "$C_7$-$C_{30}$ alkylaryl group" is preferably $C_7$-$C_{12}$ alkylaryl group. Examples of alkylaryl groups include, but are not limited to, o-tolyl, m-tolyl, p-tolyl, 2,3-xylyl, 2,4-xylyl, 2,5-xylyl, o-cumenyl, m-cumenyl, p-cumenyl, and mesityl.

In the present specification, the "$C_7$-$C_{30}$ arylalkyl group" is preferably $C_7$-$C_{12}$ arylalkyl group. Examples of arylalkyl groups include, but are not limited to, benzyl, phenethyl, diphenylmethyl, triphenylmethyl, 1-naphthylmethyl, 2-naphthylmethyl, 2,2-diphenylethyl, 3-phenylpropyl, 4-phenylbutyl, and 5-phenylpentyl.

In the present specification, the "$C_4$-$C_{30}$ cycloalkyl group" is preferably $C_4$-$C_{10}$ cycloalkyl group. Examples of cycloalkyl groups include, but are not limited to, cyclopropyl, cyclobutyl, cyclopentyl, and cyclohexyl.

In the present specification, the "$C_4$-$C_{30}$ cycloalkenyl group" is preferably $C_4$-$C_{10}$ cycloalkenyl group. Examples of cycloalkenyl groups include, but are not limited to, cyclopropenyl, cyclobutenyl, cyclopentenyl, and cyclohexenyl.

In the present specification, the "$C_1$-$C_{30}$ alkoxy group" is preferably $C_1$-$C_{10}$ alkoxy group, and more preferably $C_1$-$C_6$ alkoxy group. Examples of alkoxy groups include, but are not limited to, methoxy, ethoxy, propoxy, butoxy, and pentyloxy.

In the present specification, the "$C_6$-$C_{30}$ aryloxy group" is preferably $C_6$-$C_{10}$ aryloxy group. Examples of aryloxy groups include, but are not limited to, phenyloxy, naphthyloxy, and biphenyloxy.

In the present specification, in "alkylthio group (—$SY^1$: in the formula, $Y^1$ is a substituted or unsubstituted $C_1$-$C_{20}$ alkyl group)" and "alkylsulfonyl group (—$SO_2Y^3$: in the formula, $Y^3$ is a substituted or unsubstituted $C_1$-$C_{20}$ alkyl group)", $Y^1$ and $Y^3$ are preferably $C_1$-$C_{10}$ alkyl group, and more preferably $C_1$-$C_6$ alkyl group. Examples of alkyl groups include, but are not limited to, methyl, ethyl, propyl, isopropyl, n-butyl, sec-butyl, tert-butyl, pentyl, hexyl, and dodecanyl.

In the present specification, in "arylthio group (—$SY^2$: in the formula, $Y^2$ is a substituted or unsubstituted $C_6$-$C_{18}$ aryl group)" and "arylsulfonyl group (—$SO_2Y^4$: in the formula, $Y^4$ is a substituted or unsubstituted $C_6$-$C_{18}$ aryl group)", $Y^2$ and $Y^4$ are preferably $C_6$-$C_{10}$ aryl group. Examples of aryl groups include, but are not limited to, phenyl, 1-naphthyl, 2-naphthyl, indenyl, biphenylyl, anthryl, and phenanthryl.

"$C_1$-$C_{30}$ hydrocarbon group," "$C_1$-$C_{30}$ alkoxy group," "$C_6$-$C_{30}$ aryloxy group," "amino group," "silyl group," "alkylthio group," "arylthio group," "alkylsulfonyl group," and "arylsulfonyl group" may be substituted. Examples of substituents in these cases include ester group, carboxyl group, amide group, alkyne group, trimethylsilyl group, amino group, phosphonyl group, thio group, carbonyl group, nitro group, sulfo group, imino group, halogeno group, and alkoxy group. In these cases, one or more substituents (up to the maximum possible number) may be introduced into replaceable positions, and preferably, 1 to 4 substituents may be introduced. When the number of substituents is 2 or more, the substituents may be the same or different.

In the present specification, examples of "substituted or unsubstituted amino group" include, but are not limited to, amino, dimethylamino, methylamino, methylphenylamino, and phenylamino.

In the present specification, examples of "substituted or unsubstituted silyl group" include, but are not limited to, dimethylsilyl, diethylsilyl, trimethylsilyl, triethylsilyl, trimethoxysilyl, triethoxysilyl, diphenylmethylsilyl, triphenylsilyl, triphenoxysilyl, dimethylmethoxysilyl, dimethylphenoxysilyl, and methylmethoxyphenyl.

In the present specification, examples of "aromatic group" include phenyl group, biphenyl group, and terphenyl group.

In the present specification, examples of "heterocyclic group" include thienyl group, pyrrolyl group, pyridyl group, bipyridyl group, oxazolyl group, oxadiazolyl group, thiazolyl group, thiadiazolyl group, and terthienyl group.

In the present specification, examples of "condensed polycyclic aromatic group" include fluorenyl group, naphthyl group, fluoranthenyl group, anthryl group, phenanthryl group, pyrenyl group, tetracenyl group, pentacenyl group, triphenylenyl group, and perirenyl group.

In the present specification, examples of "condensed polycyclic heterocyclic group" include carbazolyl group, acridinyl group and phenanthroryl group.

Further, examples of substituents which can be had by these "aromatic group," "heterocyclic group," "condensed polycyclic aromatic group" and "condensed polycyclic heterocyclic group" include, but are not limited to, $C_1$-$C_{10}$ hydrocarbon group (e.g., methyl, ethyl, propyl, butyl, phenyl, naphthyl, indenyl, tolyl, xylyl and benzyl), $C_1$-$C_{10}$ alkoxy group (e.g., methoxy, ethoxy, propoxy and butoxy), $C_6$-$C_{10}$ aryloxy group (e.g., phenyloxy, naphthyloxy and biphenyloxy), amino group, hydroxyl group, halogen atom (e.g., fluorine, chlorine, bromine and iodine) and silyl group. In these cases, one or more substituents may be introduced into replaceable positions, and preferably, 1 to 4 substituents are introduced. When the number of substituents is 2 or more, the substituents may be the same or different.

2. Grignard Reagent Used in the Organic Group Addition Step A

The Grignard reagent used in the organic group addition step A in the production method of the present invention is represented by the above-described formula (3).

In formula (3), $R^3$ is not particularly limited as long as it is an organic group having an inactive substituent by which the Grignard reagent can be adjusted.

In formula (3), $R^3$ is preferably a $C_1$-$C_{20}$ alkyl group, an allyl group, a benzyl group, a 4-methoxybenzyl group, a phenyl group, a p-methoxyphenyl group, a carbazolylphenyl group, a biphenyl group, a 1-naphthyl group, a pyrenyl group, a di(alkyloxy)benzoyloxyphenyl group or the like.

Further, in formula (3), $R^3$ is preferably a naphthalene tetracarboxylic diimide derivative-containing group, an anthraquinone derivative-containing group, a tetrathiafulvalene derivative-containing group, a polythiophene derivative-containing group or the like.

In formula (3), $R^3$ is preferably a group represented by the following formula (2);

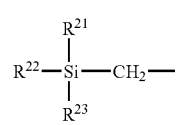

(2)

wherein $R^{21}$ to $R^{23}$ are each independently a hydrogen atom, a substituted or unsubstituted $C_1$-$C_{30}$ hydrocarbon group, a substituted or unsubstituted $C_1$-$C_{30}$ alkoxy group, a substituted or unsubstituted $C_6$-$C_{30}$ aryloxy group, a substituted or unsubstituted amino group, a substituted or unsubstituted silyl group, a substituted or unsubstituted alkylthio group (—$SY^1$: in the formula, $Y^1$ is a substituted or unsubstituted $C_1$-$C_{20}$ alkyl group), a substituted or unsubstituted arylthio group (—$SY^2$; in the formula, $Y^2$ is a substituted or unsubstituted $C_6$-$C_{18}$ aryl group), a substituted or unsubstituted alkylsulfonyl group (—$SO_2Y^3$: in the formula, $Y^3$ is a substituted or unsubstituted $C_1$-$C_{20}$ alkyl group), or a substituted or unsubstituted arylsulfonyl group (—$SO_2Y^4$: in the formula, $Y^4$ is a substituted or unsubstituted $C_6$-$C_{18}$ aryl group). Among them, $R^3$ is preferably a trimethylsilylmethyl group, an (alkyl)dimethylsilylmethyl group (e.g., a (hexyl)dimethylsilylmethyl group, and a (dodeca)dimethylsilylmethyl group), a (isopropoxy)dimethylsilylmethyl group, a (phenyl)dimethylsilyl group, a (4-methoxyphenyl)dimethylsilylmethyl group, a (4-biphenyl)dimethylsilylmethyl group, a (1-naphthyl)dimethylsilylmethyl group, a (pyrenoxyphenyl)dimethylsilylmethyl group, an ((alkyloxy)benzoyloxyphenyl)dimethylsilylmethyl group, a (di(alkyloxy)benzoyloxyphenyl)dimethylsilylmethyl group, a (terpyridinyl)dimethylsilylmethyl group, a (carbazolylphenyl)dimethylsilylmethyl group, or a (pyrenylphenyl)dimethylsilylmethyl group.

In the organic group addition step A, the Grignard reagent is used, preferably in an amount of 1 to 20 equivalents, and more preferably in an amount of 1 to 10 equivalents, of the fullerene or fullerene derivative to which the organic group is added in the organic group addition step A.

According to the preferred embodiment of the present invention, $R^3$ in the above-described formula (3) is to be added to the fullerene or fullerene derivative as the starting material.

3. Polar Substance Used in the Organic Group Addition Step A

The polar substance used in the organic group addition step A in the production method of the present invention is not particularly limited as long as it has polar properties, but the donor number (DN) of the polar substance is preferably 25 or more.

As the polar substance used in the production method of the present invention, an aprotic solvent is preferred, and it is more preferred to use N,N-dimethylformamide (DMF), dimethyl sulfoxide (DMSO), pyridine or the like. Among them, N,N-dimethylformamide is particularly preferably used since the yield of a fullerene derivative obtained becomes higher.

In the organic group addition step A, the polar substance is used, preferably in an amount of 3 to 100 equivalents, more preferably in an amount of 5 to 60 equivalents, and particularly preferably in an amount of 10 to 50 equivalents, of the fullerene or fullerene derivative to which the organic group is added in the organic group addition step A, since the yield of a fullerene derivative obtained becomes higher.

4. Production of Fullerene Derivative Using the Organic Group Addition Step A

With the fullerene or fullerene derivative to which the organic group is added in the organic group addition step A, at least the Grignard reagent and the polar substance are reacted to add the organic group, thereby producing a fullerene derivative.

The reaction in the organic group addition step A is preferably performed using a solvent. As the solvent, for example, toluene, tetrahydrofuran, dichlorobenzene, a mixed solvent thereof or the like is used. Among them, dichlorobenzene is preferably used as the solvent.

In order to accelerate the reaction in the organic group addition step A, various additives may be used depending on various purposes. Types of catalysts and additives are not particularly limited, and may be suitably selected depending on the type of the starting material or a fullerene derivative to be produced (type of group to be added).

The reaction system for reacting the Grignard reagent and the polar substance with the fullerene or fullerene derivative may be any reaction system, and any of a closed-type system, open-type system and gas-flow-type system may be employed. Further, the reaction method is not particularly limited, and may be appropriately selected in view of types, amounts, etc. of fullerene, fullerene derivative, Grignard reagent and polar substance to be used.

The addition order of the fullerene or fullerene derivative, the Grignard reagent and the polar substance to a reaction tank and the method for the addition thereof may be optionally selected. However, it is preferred that the polar substance is added to a solvent in which the fullerene or fullerene derivative has been dissolved, and thereafter adding the Gingnard reagent thereto.

The reaction temperature is generally in the range of –70 to 70° C., and preferably in the range of –50 to 50° C. There is a tendency that, when the reaction temperature is too low, the reaction rate is insufficient, and when the reaction temperature is too high, a side reaction preferentially occurs. The reaction pressure is not particularly limited, and may be ordinary pressure or high pressure. However, ordinary pressure is preferred. The reaction time may be suitably selected depending on the types of the fullerene and organometallic compound to be used, the type of the solvent, the type of the oxidant, the reaction method, etc. In general, the reaction is performed for 2 minutes to 2 hours, and preferably for 5 minutes to 1 hour.

The termination of the reaction is performed, for example, by adding aqueous ammonium chloride solution or the like to the reaction system.

In the organic group addition step A of the present invention, by reacting the Grignard reagent and the polar substance with the fullerene or fullerene derivative, an adduct of fullerene (e.g., a mono(organo)fullerene derivative, a di(organo)fullerene derivative, a tri(organo)fullerene derivative, and a tetra(organo)fullerene derivative) can be selectively produced.

The fullerene derivative produced by the reaction is not required to be purified if the selective production rate thereof is high. However, there is a case where the fullerene derivative is obtained as a crude product in which by-products such as the raw material fullerene, a slight amount of hydroalkylated body and oxide are mixed therewith. Therefore, it is preferred that a fullerene derivative to which a predetermined organic group has been added is isolated/purified from the crude product. Examples of techniques for isolating/purifying a fullerene derivative produced include a technique utilizing chromatography such as HPLC and column chromatography, and a technique of solvent extraction using an organic solvent or the like.

When a fullerene derivative to which an organic group has been added is used as the fullerene derivative to which the organic group is added in the organic group addition step A, according to the preferred embodiment of the organic group addition step A of the present invention, the organic group to be added can be added to a specific position. Specifically, when a fullerene derivative represented by the above-described formula (1) in which an organic group has been added to 1 to 4 carbons among 5 carbons positioned at A to E is used as the starting material, an organic group is newly added to carbons positioned at A to E, to which no organic group has been added, in the organic group addition step A of the present invention.

5. Fullerene Derivative Produced by the Organic Group Addition Step A

The fullerene derivative produced in the organic group addition step A is not particularly limited as long as the organic group is added to carbons constituting a fullerene. However, according to the preferred embodiment of the present invention, a fullerene derivative represented by the above-described formula (1A) is produced.

In the fullerene derivative represented by the above-described formula (1A) produced in the organic group addition step A, it is preferred that organic groups, which are added to 1 to 5 carbons among 5 carbons positioned at A to E, are each independently a hydrogen atom, a substituted or unsubstituted $C_1$-$C_{30}$ hydrocarbon group, a substituted or unsubstituted $C_1$-$C_{30}$ alkoxy group, a substituted or unsubstituted $C_6$-$C_{30}$ aryloxy group, a substituted or unsubstituted amino group, a substituted or unsubstituted silyl group, a substituted or unsubstituted alkylthio group (—$SY^1$: in the formula, $Y^1$ is a substituted or unsubstituted $C_1$-$C_{20}$ alkyl group), a substituted or unsubstituted arylthio group (—$SY^2$: in the formula, $Y^2$ is a substituted or unsubstituted $C_6$-$C_{18}$ aryl group), a substituted or unsubstituted alkylsulfonyl group (—$SO_2Y^3$: in the formula, $Y^3$ is a substituted or unsubstituted $C_1$-$C_{20}$ alkyl group), or a substituted or unsubstituted arylsulfonyl group (—$SO_2Y^4$: in the formula, $Y^4$ is a substituted or unsubstituted $C_6$-$C_{18}$ aryl group). Among them, a $C_1$-$C_{20}$ alkyl group, an allyl group, a benzyl group, a 4-methoxybenzyl group, a phenyl group, a p-methoxyphenyl group, a carbazolylphenyl group, a biphenyl group, a 1-naphthyl group, a pyrenyl group, or a di(alkyloxy)benzoyloxyphenyl group is preferred.

In the fullerene derivative represented by the above-described formula (1A) produced in the organic group addition step A, it is preferred that organic groups, which are added to 1 to 5 carbons among 5 carbons positioned at A to E, are each independently a naphthalene tetracarboxylic diimide derivative-containing group, an anthraquinone derivative-containing group, a tetrathiafulvalene derivative-containing group, or a polythiophene derivative-containing group.

Further, in the fullerene derivative represented by the above-described formula (1A) produced in the organic group addition step A, it is preferred that organic groups, which are added to 1 to 5 carbons among 5 carbons positioned at A to E, are each independently a group represented by the following formula (2):

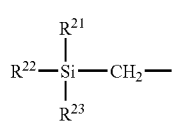

(2)

wherein $R^{21}$ to $R^{23}$ are each independently a hydrogen atom, a substituted or unsubstituted $C_1$-$C_{30}$ hydrocarbon group, a substituted or unsubstituted $C_1$-$C_{30}$ alkoxy group, a substituted or unsubstituted $C_6$-$C_{30}$ aryloxy group, a substituted or unsubstituted amino group, a substituted or unsubstituted silyl group, a substituted or unsubstituted alkylthio group (—$SY^1$: in the formula, $Y^1$ is a substituted or unsubstituted $C_1$-$C_{20}$ alkyl group), a substituted or unsubstituted arylthio group (—$SY^2$: in the formula, $Y^2$ is a substituted or unsubstituted $C_6$-$C_{18}$ aryl group), a substituted or unsubstituted alkylsulfonyl group (—$SO_2Y^3$: in the formula, $Y^3$ is a substituted or unsubstituted $C_1$-$C_{20}$ alkyl group), or a substituted or unsubstituted arylsulfonyl group (—$SO_2Y^4$: in the formula, $Y^4$ is a substituted or unsubstituted $C_6$-$C_{18}$ aryl group). Among them, a trimethylsilylmethyl group, an (alkyl)dimethylsilylmethyl group (e.g., a (hexyl)dimethylsilylmethyl group, and a (dodeca)dimethylsilylmethyl group), a (isopropoxy)dimethylsilylmethyl group, a (phenyl)dimethylsilyl group, a (4-methoxyphenyl)dimethylsilylmethyl group, a (4-biphenyl)dimethylsilylmethyl group, a (1-naphthyl)dimethylsilylmethyl group, a (pyrenoxyphenyl)dimethylsilylmethyl group, an ((alkyloxy)benzoyloxyphenyl)dimethylsilylmethyl group, a (di(alkyloxy)benzoyloxyphenyl)dimethylsilylmethyl group, a (terpyridinyl)dimethylsilylmethyl group, a (carbazolylphenyl)dimethylsilylmethyl group, or a (pyrenylphenyl)dimethylsilylmethyl group is preferred.

II. Organic Group Addition Step B

The organic group addition step B of the present invention is a step of reacting at least a basic compound and a halogen compound with a fullerene derivative to which a hydrogen atom has been added to dehydrogenate the fullerene derivative and to add an organic group to the fullerene derivative.

1. Fullerene Derivative to which Organic Group is Added in the Organic Group Addition Step B The fullerene derivative to which the organic group is added in the organic group addition step B is a fullerene derivative to which a hydrogen atom and an organic group have been added in the organic group addition step A.

2. Basic Compound Used in the Organic Group Addition Step B

The basic compound to be used in the organic group addition step B in the production method of the present invention is not particularly limited as long as it is a compound having basicity.

As the basic compound to be used in the organic group addition step B, a metal hydride (e.g., KH, NaH, $CaH_2$), a metal alkoxide (t-BuOK (potassium t-butoxide), t-BuONa (sodium t-butoxide)), an alkali metal reagent (e.g., BuLi), an alkali metal (e.g., K, Na, Li) or an organic alkali (e.g., tetrabutylammonium hydroxide) is preferably used. Among them, a metal alkoxide including Na or K is preferred, and t-BuOK or t-BuONa is particularly preferred.

In the organic group addition step B, the basic compound is used preferably in an amount of 1 to 3 equivalents, and more preferably in an amount of 1 to 2 equivalents of the fullerene derivative to which the organic group is added in the organic group addition step B, since the yield of a fullerene derivative obtained becomes higher.

3. Halogen Compound Used in the Organic Group Addition Step B

The halogen compound to be used in the organic group addition step B in the production method of the present invention is preferably a compound represented by the above-described formula (4). In formula (4), $R^4$ is preferably a $C_1$-$C_{30}$ alkyl group, an allyl group, a benzyl group, a 4-methoxybenzyl group, a phenyl group, a p-methoxyphenyl group, a carbazolylphenyl group, a biphenyl group, a 1-naphthyl group, a pyrenyl group, or a di(alkyloxy)benzoyloxyphenyl group.

Further, in formula (4), $R^4$ is preferably a naphthalene tetracarboxylic diimide derivative-containing group, an anthraquinone derivative-containing group, a tetrathiafulvalene derivative-containing group, a polythiophene derivative-containing group or the like.

In formula (4), $R^4$ is preferably a group represented by the following formula (2):

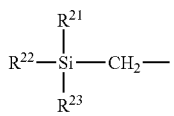

(2)

wherein $R^{21}$ to $R^{23}$ are each independently a hydrogen atom, a substituted or unsubstituted $C_1$-$C_{30}$ hydrocarbon group, a substituted or unsubstituted $C_1$-$C_{30}$ alkoxy group, a substituted or unsubstituted $C_6$-$C_{30}$ aryloxy group, a substituted or unsubstituted amino group, a substituted or unsubstituted silyl group, a substituted or unsubstituted alkylthio group (—$SY^1$: in the formula, $Y^1$ is a substituted or unsubstituted $C_1$-$C_{20}$ alkyl group), a substituted or unsubstituted arylthio group (—$SY^2$: in the formula, $Y^2$ is a substituted or unsubstituted $C_6$-$C_{18}$ aryl group), a substituted or unsubstituted alkylsulfonyl group (—$(SO)_2Y^3$: in the formula, $Y^3$ is a substituted or unsubstituted $C_1$-$C_{20}$ alkyl group), or a substituted or unsubstituted arylsulfonyl group (—$SO_2Y^4$: in the formula, $Y^4$ is a substituted or unsubstituted $C_6$-$C_{18}$ aryl group). Among them, $R^4$ is preferably a trimethylsilylmethyl group, an (alkyl)dimethylsilylmethyl group (e.g., a (hexyl) dimethylsilylmethyl group, and a (dodeca)dimethylsilylmethyl group), a (isopropoxy)dimethylsilylmethyl group, a (phenyl)dimethylsilyl group, a (4-methoxyphenyl)dimethylsilylmethyl group, a (4-biphenyl)dimethylsilylmethyl group, a (1-naphthyl)dimethylsilylmethyl group, a (pyrenoxyphenyl)dimethylsilylmethyl group, an ((alkyloxy)benzoyloxyphenyl)dimethylsilylmethyl group, a (di(alkyloxy)benzoyloxyphenyl)dimethylsilylmethyl group, a (terpyridinyl)dimethylsilylmethyl group, a (carbazolylphenyl)dimethylsilylmethyl group, a (pyrenylphenyl)dimethylsilylmethyl group or the like.

According to the preferred embodiment of the present invention, $R^4$ in the above-described formula (4) is to be added to the fullerene derivative to which the organic group is added in the organic group addition step B.

In the organic group addition step B, the halogen compound is used preferably in an amount of 5 to 100 equivalents, and more preferably in an amount of 10 to 50 equivalents of the fullerene derivative to which the organic group is added in the organic group addition step B, since the yield of a fullerene derivative obtained becomes higher.

4. Production of Fullerene Derivative Using the Organic Group Addition Step B

With a fullerene derivative to which a hydrogen atom has been added (starting material), at least the basic compound and the halogen compound are reacted, thereby adding an organic group to the fullerene derivative (organic group addition step B).

The reaction in the organic group addition step B is preferably performed under inert gas atmosphere using a solvent. As the solvent, a solvent which can dissolve the fullerene derivative as the starting material is preferred, and examples thereof include benzonitrile.

In order to accelerate the reaction in the organic group addition step B, various additives may be used depending on various purposes. Types of catalysts and additives are not particularly limited, and may be suitably selected depending on the type of the starting material or a fullerene derivative to be produced (type of group to be added).

The reaction system for reacting the basic compound and the halogen compound with the fullerene or fullerene derivative may be any reaction system, and any of a closed-type system, open-type system and gas-flow-type system may be employed. Further, the reaction method is not particularly limited, and may be appropriately selected in view of types, amounts, etc. of fullerene derivative, basic compound and halogen compound to be used.

The addition order of the fullerene derivative (starting material), basic compound and halogen compound to a reaction tank and the method for the addition thereof may be optionally selected. However, it is preferred that the basic compound is added to a solvent in which the fullerene derivative has been dissolved, and thereafter adding the halogen compound thereto. According to the preferred embodiment of the organic group addition step B of the present invention, the basic compound is added dropwise to the solvent in which the fullerene derivative has been dissolved and the mixture is stirred for 5 to 20 minutes, and after that, the halogen compound is added thereto to cause a reaction in the temperature range of generally 20 to 180° C., and preferably 50 to 150° C., for 2 to 12 hours, and preferably 4 to 10 hours. The reaction pressure is not particularly limited, and may be near ordinary pressure or high pressure. However, near ordinary pressure is preferred.

In the organic group addition step B of the present invention, by reacting the Grignard reagent and the polar substance with the fullerene or fullerene derivative, a multiple adduct of fullerene (e.g., a mono(organo)fullerene derivative, a di(organo)fullerene derivative, a tri(organo)fullerene derivative, and a tetra(organo)fullerene derivative) can be selectively produced.

Further, it is preferred that a fullerene derivative produced is isolated/purified, and the technique thereof is the same as that in the organic group addition step A.

According to the preferred embodiment of the organic group addition step B of the present invention, the organic group to be added can be added to a specific position. Specifically, when a fullerene derivative represented by the above-described formula (1A) is used as the starting material, according to the organic group addition step B of the present invention, an organic group is newly added to carbons positioned at A to E, to which no organic group has been added. That is, a new organic group is added to 5 carbon atoms located around carbon atoms constituting a pentagon shape including those to which a hydrogen atom has been added.

The fullerene derivative produced by the reaction is not required to be purified if the selective production rate thereof is high. However, purification thereof may be carried out using a technique utilizing chromatography such as HPLC and column chromatography, a technique of solvent extraction using an organic solvent or the like, etc.

5. Fullerene Derivative Produced in the Organic Group Addition Step B

The fullerene derivative produced in the organic group addition step B is not particularly limited as long as the organic group has been added to carbon(s) constituting the fullerene, but according to the preferred embodiment of the present invention, a fullerene derivative represented by the following formula (1B) is produced:

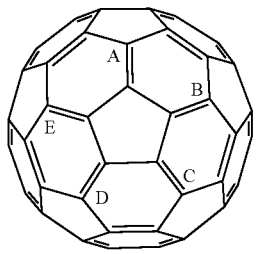

(IB)

Regarding the fullerene derivative represented by the above-described formula (1B) produced in the organic group addition step B, examples of organic groups added to 1 to 5 carbons among 5 carbons positioned at A to E are the same as the examples of the organic groups added to the carbons positioned at A to E in formula (1A).

EXAMPLES

Hereinafter, the present invention will be specifically described by way of examples, but the present invention is not limited thereby.

Example 1

Production of $C_{60}(CH_2Si(CH_3)_3)H$

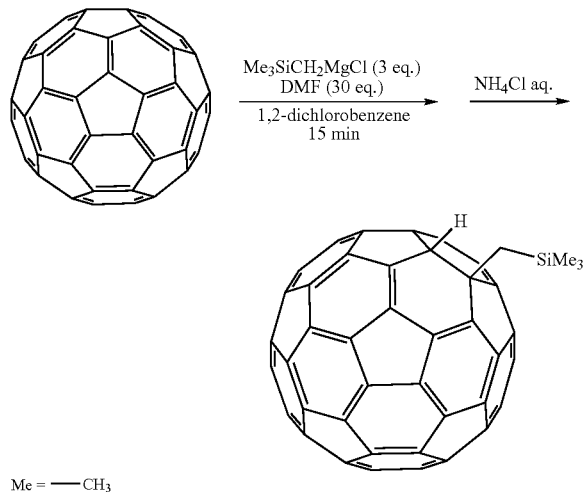

Scheme 1

As indicated in Scheme 1 above, fullerene $C_{60}$ (400 mg, 0.555 mmol) was dissolved in o-dichlorobenzene (100 mL) under nitrogen atmosphere at room temperature, and N,N-dimethylformamide (DMF) was added thereto in an amount of 30 equivalents of the fullerene (1.29 mL, 16.7 mmol). $Me_3SiCH_2MgCl$ in tetrahydrofuran (THF) solution was added dropwise to the obtained purple solution using a syringe in an amount of 3 equivalents of the fullerene (2.81 mL, 0.592 M, 1.67 mmol). The mixture was stirred for 10 minutes, and to the obtained brow-black solution, saturated ammonium chloride solution (0.2 mL) was added to terminate the reaction. The obtained reaction mixture was passed through a short-pass silica gel column using toluene as a developing solvent to remove by-products such as magnesium salt, and after that, purification was carried out by high-performance liquid chromatography (HPLC) (column: Buckyprep manufactured by Nakalai Tesque, 20 mm×250 mm, eluting solution: toluene/2-propanol=7/3). Fractions of $C_{60}(CH_2Si(CH_3)_3)H$ were collected and concentrated, and thereafter methanol was added thereto to precipitate fullerene derivative $C_{60}(CH_2Si(CH_3)_3)H$. By filtration and drying, $C_{60}(CH_2Si(CH_3)_3)H$ was obtained (isolated yield: 93%).

Regarding the obtained fullerene derivative $C_{60}(CH_2Si(CH_3)_3)H$, the measurement of APCI-HRMS utilizing $^1H$ NMR, $^{13}C$ NMR and TOF method was carried out. Results are shown below:

$^1H$ NMR (400 MHz, $CDCl_3/CS_2$): δ 0.604 (s, 9H, SiMe), 2.96 (s, 2H, $CH_2$), 6.46 (s, 1H, $C_{60}H$);

$^{13}C$ NMR (100 MHz, $CDCl_3/CS_2$): δ 0.819 (3C, $SiCH_3$), 38.96 (1C, $CH_2$), 61.72 (1C, $C_{60}H$), 62.28 (1C, $C_{60}CH_2$), 134.76 (2C, $C_{60}$), 136.57 (2C, $C_{60}$), 140.07 (2C, $C_{60}$), 140.30 (2C, $C_{60}$), 141.61 (2C, $C_{60}$), 141.62 (2C, $C_{60}$), 141.92 (2C, $C_{60}$), 141.99 (2C, $C_{60}$), 142.01 (2C, $C_{60}$), 142.07 (2C, $C_{60}$), 142.51 (2C, $C_{60}$), 142.52 (2C, $C_{60}$), 143.25 (2C, $C_{60}$), 144.63 (2C, $C_{60}$), 144.67 (2C, $C_{60}$), 145.25 (2C, $C_{60}$), 145.31 (2C, $C_{60}$), 145.36 (2C, $C_{60}$), 145.41 (2C, $C_{60}$), 145.59 (2C, $C_{60}$), 145.81 (2C, $C_{60}$), 146.14 (2C, $C_{60}$), 146.17 (2C, $C_{60}$), 146.24 (2C, $C_{60}$), 146.36 (2C, $C_{60}$), 149.90 (2C, $C_{60}$), 147.30 (1C, $C_{60}$), 147.42 (1C, $C_{60}$), 153.99 (2C, $C_{60}$), 158.07 (2C, $C_{60}$);

APCI-HRMS (−): calcd for $C_{64}H_{11}Si$ (M−H$^+$), 807.06300; found, 807.05929.

Examples 2 to 4, Comparative Example 1

$C_{60}(CH_2Si(CH_3)_3)H$ was synthesized under the same conditions as those of Example 1, except that DMF was used in an amount of 3 equivalents of the fullerene as the starting material (Example 2).

$C_{60}(CH_2Si(CH_3)_3)H$ was synthesized under the same conditions as those of Example 1, except that DMF was used in an amount of 10 equivalents of the fullerene as the starting material (Example 3).

$C_{60}(CH_2Si(CH_3)_3)H$ was synthesized under the same conditions as those of Example 1, except that DMF was used in an amount of 100 equivalents of the fullerene as the starting material (Example 4).

$C_{60}(CH_2Si(CH_3)_3)H$ was synthesized under the same conditions as those of Example 1, except that no DMF was used (Comparative Example 1).

In Examples 1 to 4 and Comparative Example 1, as the standard sample, $C_{60}(Ph)_5H$ (4.98 mM/o-dichlorobenzene solution) was used. Analysis was carried out utilizing high-performance liquid chromatography: HPLC (column: Buckyprep manufactured by Nakalai Tesque, eluting solution: toluene/2-propanol=7/3), and yields of $C_{60}$ and $C_{60}(CH_2Si(CH_3)_3)H$ were measured. Results are shown below:

TABLE 1

|  | DMF equivalent | Yield of product (HPLC) | Collection rate of fullerene (HPLC) |
| --- | --- | --- | --- |
| Comparative Example 1 | 0 eq. | 10% | 63% |
| Example 2 | 3 eq. | 47% | 49% |
| Example 3 | 10 eq. | 82% | 17% |
| Example 1 | 30 eq. | 91% | 7% |
| Example 4 | 100 eq. | 86% | 9% |

Next, the relationship between the donor number (DN) of the polar substance and the ratio of adduct added to fullerene $C_{60}$ (yield of product) was examined. Specifically, in addition to the aforementioned test example in which DMF was used as the polar substance, a test example using dimethyl sulfoxide (DMSO), a test example using pyridine, and a test example using ethanol were carried out. In these 4 test examples, $C_{60}(CH_2Si(CH_3)_3)H$ was synthesized from $C_{60}$, and analysis thereof was carried out using HPLC as in the case described above, thereby examining the yield of product and the collection rate of fullerene. The method for synthesizing $C_{60}(CH_2Si(CH_3)_3)H$ was the same as that in the aforementioned step. Results are shown in Table 2.

TABLE 2

| Polar substance used | Donor number | Additive amount (equivalent) | Yield of product (HPLC) | Collection rate of fullerene (HPLC) |
| --- | --- | --- | --- | --- |
| DMF | 26.6 | 30 eq. | 91% | 7% |
| DMSO | 29.8 | 30 eq. | 83% | 14% |
| Pyridine | 33.1 | 30 eq. | 40% | 47% |
| Ethanol | 20.0 | 30 eq. | 2% | 88% |

Based on the results, it was found that there is a tendency that the yield of a product becomes higher when a polar substance which is aprotic and has a higher donor number is used in the organic group addition step A.

Example 5

Production of $C_{60}(CH_2Si(CH_3)_3)_2$

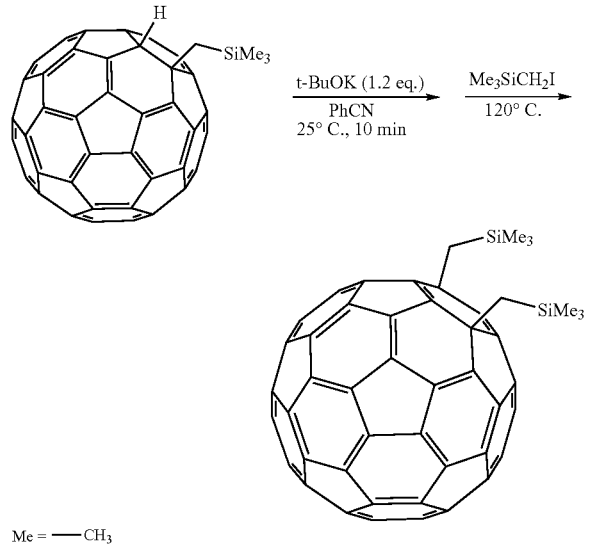

The fullerene derivative $C_{60}(CH_2Si(CH_3)_3)H$ (300 mg, 0.371 mmol) produced in Example 1 was dissolved in benzonitrile (60 mL) and potassium t-butoxide (t-BuOK) in THF solution (0.445 mL, 0.445 mmol) was added dropwise thereto, and the mixture was stirred for 10 minutes. To the obtained brown-black solution, $Me_3SiCH_2I$ (1.10 mL, 7.42 mmol) was added, and the mixture was heated to 120° C. and stirred for 8 hours. After the solvent was distilled away under reduced pressure, purification was carried out using silica gel column chromatography (eluting solution: carbon disulfide/hexane=½). Fractions of fullerene derivative $C_{60}(CH_2Si(CH_3)_3)_2$ were collected and concentrated, and thereafter methanol was added thereto to precipitate $C_{60}(CH_2Si(CH_3)_3)_2$. By filtration and drying, $C_{60}(CH_2Si(CH_3)_3)_2$ was obtained (isolated yield: 93%).

Regarding the obtained fullerene derivative $C_{60}(CH_2Si(CH_3)_3)_2$, the measurement of APCI-HRMS utilizing $^1H$ NMR, $^{13}C$ NMR and TOF method was carried out. Results are shown below:

$^1H$ NMR (400 MHz, $CDCl_3$): δ 0.40 (s, 18H, SiMe), 2.47 (d, 2H, $^2J$=15 Hz, $CH_2$), 2.61 (d, 2H, $^2J$=15 Hz, $CH_2$);

$^{13}C$ NMR (100 MHz, $CDCl_3$): δ 0.704 (6C, SiMe), 33.94 (2C, $CH_2$), 56.28 (2C, $CCH_2$), 138.42 (2C, $C_{60}$), 138.79 (2C, $C_{60}$), 140.85 (1C, $C_{60}$), 141.91 (2C, $C_{60}$), 141.95 (1C, $C_{60}$), 142.63 (2C, $C_{60}$), 142.68 (1C, $C_{60}$), 142.70 (2C, $C_{60}$), 142.92 (2C, $C_{60}$), 143.12 (2C, $C_{60}$), 143.28 (2C, $C_{60}$), 143.58 (2C, $C_{60}$), 143.79 (2C, $C_{60}$), 144.12 (2C, $C_{60}$), 144.25 (2C, $C_{60}$), 144.28 (2C, $C_{60}$), 144.50 (2C, $C_{60}$), 144.58 (1C, $C_{60}$), 144.74 (2C, $C_{60}$), 145.01 (2C, $C_{60}$), 145.10 (2C, $C_{60}$), 145.45 (2C, $C_{60}$), 146.83 (2C, $C_{60}$), 146.98 (2C, $C_{60}$), 147.13 (2C, $C_{60}$), 147.45 (2C, $C_{60}$), 147.54 (2C, $C_{60}$), 148.03 (2C, $C_{60}$), 148.59 (2C, $C_{60}$), 153.80 (2C, $C_{60}$), 158.06 (2C, $C_{60}$);

APCI-HRMS (-): calcd for $C_{68}H_{22}Si_2$ (M–H$^+$), 894.12600; found, 894.12492.

Example 6

Production of $C_{60}(CH_2Si(CH_3)_3)_3H$

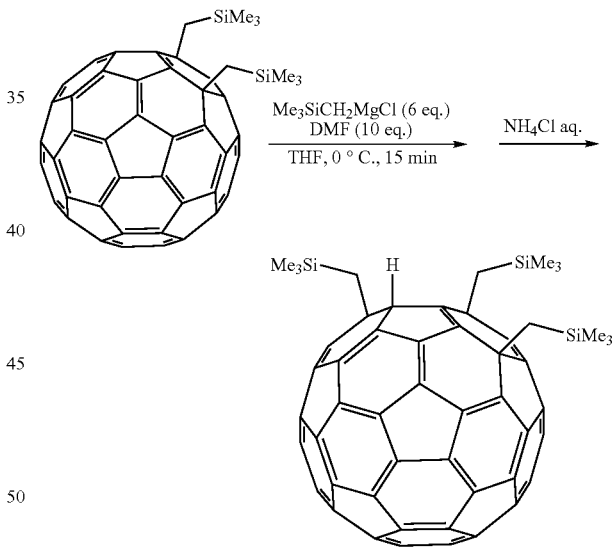

As indicated in Scheme 3 above, $C_{60}(CH_2Si(CH_3)_3)_2$ (100 mg, 0.112 mmol) produced in Example 5 was dissolved in THF (100 mL) under nitrogen atmosphere at 0° C., and DMF (86.7 μL, 1.12 mmol) was added thereto. To the obtained brownish solution, $Me_3SiCH_2MgCl$ in THF solution (1.13 mL, 0.592 M, 0.670 mmol) was slowly added dropwise using a syringe. After stirring for 15 minutes, to the obtained brown-black solution, saturated ammonium chloride solution (0.1 mL) was added to terminate the reaction. The obtained reaction mixture was passed through a short-pass silica gel column using toluene as a developing solvent to remove by-products such as magnesium salt. After the solvent was distilled away under reduced pressure, purification was carried out by silica gel column chromatography (eluting solution: carbon disulfide/hexane=1/1). Fractions of the title compound were collected and concentrated, and thereafter methanol was added thereto to precipitate the product of interest. By filtration and drying, the title compound was obtained (isolated yield: 64%).

Regarding the obtained fullerene derivative $C_{60}(CH_2Si(CH_3)_3)_3H$, the measurement of APCI-HRMS utilizing $^1H$ NMR, $^{13}C$ NMR and TOF method was carried out. Results are shown below:

$^1H$ NMR (400 MHz, CDCl$_3$): δ 0.222 (s, 9H, SiMe$_3$), 0.285 (s, 9H, SiMe$_3$), 0.288 (s, 9H, SiMe$_3$), 2.05 (d, 1H, $^2J$=14.2 Hz, CH$_2$), 2.23 (d, $^2J$=14.6 Hz, 1H, CH$_2$), 2.29 (d, $^2J$=14.2 Hz, 1H, CH$_2$), 2.28 (d, $^2J$=14.6 Hz, 1H, CH$_2$), 2.37 (d, $^2J$=14.6 Hz, 1H, CH$_2$), 2.40 (d, $^2J$=14.6 Hz, 1H, CH$_2$), 5.29 (s, 1H, C$_{60}$H);

$^{13}C$ NMR (100 MHz, CDCl$_3$): δ 0.492 (3C, SiMe$_3$), 0.540 (3C, SiMe$_3$), 0.788 (3C, SiMe$_3$), 31.92 (1C, CH$_2$), 32.53 (1C, CH$_2$), 37.97 (1C, CH$_2$), 52.86 (1C, C$_{60}$), 54.91 (1C, C$_{60}$), 56.79 (1C, C$_{60}$), 61.88 (1C, C$_{60}$), 133.81 (1C, C$_{60}$), 134.80 (1C, C$_{60}$), 136.56 (1C, C$_{60}$), 137.84 (1C, C$_{60}$), 140.31 (1C, C$_{60}$), 140.66 (1C, C$_{60}$), 141.35 (1C, C$_{60}$), 141.78 (1C, C$_{60}$), 142.50 (1C, C$_{60}$), 142.59 (1C, C$_{60}$), 142.71 (1C, C$_{60}$), 142.87 (1C, C$_{60}$), 143.32 (1C, C$_{60}$), 143.66 (1C, C$_{60}$), 143.75 (1C, C$_{60}$), 143.91 (1C, C$_{60}$), 144.35 (1C, C$_{60}$), 144.37 (1C, C$_{60}$), 144.45 (1C, C$_{60}$), 144.50 (1C, C$_{60}$), 144.54 (1C, C$_{60}$), 144.69 (1C, C$_{60}$), 144.76 (1C, C$_{60}$), 144.78 (1C, C$_{60}$), 145.06 (1C, C$_{60}$), 145.23 (1C, C$_{60}$), 145.26 (1C, C$_{60}$), 145.37 (1C, C$_{60}$), 145.60 (1C, C$_{60}$), 145.75 (1C, C$_{60}$), 145.77 (1C, C$_{60}$), 146.41 (1C, C$_{60}$), 146.48 (1C, C$_{60}$), 146.52 (1C, C$_{60}$), 146.55 (1C, C$_{60}$), 146.69 (1C–1C, C$_{60}$), 146.79 (1C, C$_{60}$), 146.87 (1C, C$_{60}$), 147.40 (1C, C$_{60}$), 147.41 (1C, C$_{60}$), 147.62 (1C, C$_{60}$), 147.63 (1C, C$_{60}$), 147.78 (1C, C$_{60}$), 148.65 (1C, C$_{60}$), 149.01 (1C, C$_{60}$), 149.18 (1C, C$_{60}$), 149.45 (1C, C$_{60}$), 150.03 (1C, C$_{60}$), 152.35 (1C, C$_{60}$), 155.03 (1C, C$_{60}$), 156.27 (1C, C$_{60}$), 157.00 (1C, C$_{60}$), 158.41 (1C, C$_{60}$), 159.94 (1C, C$_{60}$), 162.94 (1C, C$_{60}$);

APCI-HRMS (−): calcd for $C_{72}H_{33}Si_3$ (M−H$^+$), 981.18900; found, 981.18524.

Example 7

Production of $C_{60}(Si(C_6H_5)(CH_3)_2)H$

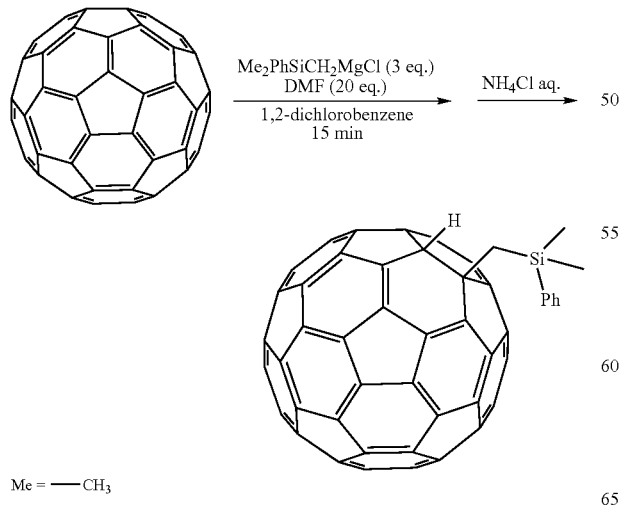

Scheme 4

As indicated in Scheme 4, the fullerene derivative $C_{60}(Si(C_6H_5)(CH_3)_2)H$ was synthesized in a manner similar to that in Example 1 except that Me$_2$PhSiCH$_2$MgCl (3.04 mL, 0.550 M, 1.67 mmol) was used in an amount of 3 equivalents of the fullerene instead of Me$_3$SiCH$_2$MgCl and N,N-dimethylformamide (DMF) was used in an amount of 20 equivalents of the fullerene (415 mg, isolated yield: 86%).

Regarding the fullerene derivative, the measurement of APCI-HRMS utilizing $^1H$ NMR, $^{13}C$ NMR and TOF method was carried out. Results are shown below:

$^1H$ NMR (500 MHz, CDCl$_3$): δ 0.892 (s, 6H, SiMe), 3.16 (s, 2H, CH$_2$), 6.39 (s, 1H, C$_{60}$H), 7.44-7.46 (m, 3H, Ph), 7.88-7.90 (m, 2H, Ph);

$^{13}C$ NMR (125 MHz, CDCl$_3$): δ −0.752 (2C, SiCH$_3$), 38.03 (1C, CH$_2$), 61.57 (1C, C$_{60}$H), 62.23 (1C, C$_{60}$CH$_2$), 128.19 (2C, Ph), 129.68 (1C, Ph), 134.16 (2C, Ph), 134.89 (2C, C$_{60}$), 136.57 (2C, C$_{60}$), 138.22 (1C, Ph), 140.05 (2C, C$_{60}$), 140.20 (2C, C$_{60}$), 141.63 (2C, C$_{60}$), 141.64 (2C, C$_{60}$), 141.94 (2C, C$_{60}$), 141.97 (2C, C$_{60}$), 142.03 (2C, C$_{60}$), 142.06 (2C, C$_{60}$), 142.54 (2C+2C, C$_{60}$), 143.27 (2C, C$_{60}$), 144.66 (2C, C$_{60}$), 144.71 (2C, C$_{60}$), 145.28 (2C, C$_{60}$), 145.36 (2C, C$_{60}$), 145.39 (2C+2C, C$_{60}$) 145.64 (2C, C$_{60}$), 145.88 (2C, C$_{60}$), 146.18 (2C, C$_{60}$), 146.22 (2C, C$_{60}$), 146.30 (2C, C$_{60}$), 146.41 (2C, C$_{60}$), 149.92 (2C, C$_{60}$), 147.35 (1C, C$_{60}$), 147.49 (1C, C$_{60}$), 154.05 (2C, C$_{60}$), 157.86 (2C, C$_{60}$);

APCI-HRMS (−): calcd for $C_{69}H_{13}Si$ (M−H$^+$), 869.07865; found, 869.07425.

Example 8

Production of $C_{60}(CH_2SiMe_2(i\text{-}PrO))H$

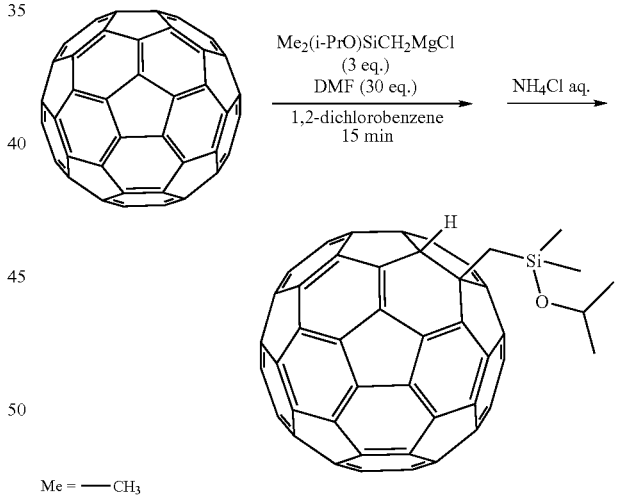

Scheme 5

As indicated in Scheme 5, the fullerene derivative $C_{60}(CH_2SiMe_2(i\text{-}PrO))H$ was synthesized in a manner similar to that in Example 1 except that Me$_2$(i-PrO)SiCH$_2$MgCl (2.69 mL, 0.620 M, 1.67 mmol) was used in an amount of 3 equivalents of the fullerene instead of Me$_3$SiCH$_2$MgCl. The obtained fullerene derivative was purified using silica gel column chromatography (eluting solution: carbon disulfide/hexane=5/3) (422 mg, isolated yield: 89%).

Regarding the obtained fullerene derivative $C_{60}(CH_2SiMe_2(i\text{-}PrO))H$, the measurement of APCI-HRMS utilizing $^1H$ NMR, $^{13}C$ NMR and TOF method was carried out. Results are shown below:

$^1$H NMR (500 MHz, CDCl$_3$): δ 0.664 (s, 6H, CH$_2$SiCH$_3$), 1.36 (d, J=6.10 Hz, 6H, CHCH$_3$), 2.95 (s, 2H, CH$_2$), 4.38 (m, J=6.10, 1H, CHCH$_3$), 6.82 (s, 1H, C$_{60}$H);

$^{13}$C NMR (125 MHz, THF-d$_8$): δ 1.023 (2C, SiMe$_2$), 26.38 (2C, CHCH$_3$), 38.49 (1C, CH$_2$), 62.36 (1C, C$_{60}$H), 63.04 (1C, CCH$_2$), 66.72 (1C, CHCH$_3$), 136.10 (2C, C$_{60}$), 137.55 (2C, C$_{60}$), 140.88 (2C, C$_{60}$), 141.03 (2C, C$_{60}$), 142.45 (2C, C$_{60}$), 142.48 (2C, C$_{60}$), 142.83 (2C, C$_{60}$), 142.91 (2C, C$_{60}$), 142.99 (2C, C$_{60}$), 143.14 (2C, C$_{60}$), 143,38 (2C+2C, C$_{60}$), 144.14 (2C, C$_{60}$), 145.58 (2C, C$_{60}$), 145.67 (2C, C$_{60}$), 146.12 (2C, C$_{60}$), 146.17 (2C, C$_{60}$), 146.22 (2C, C$_{60}$), 146.23 (2C, C$_{60}$), 146.90 (2C, C$_{60}$), 147.03 (2C+2C, C$_{60}$), 147.04 (2C, C$_{60}$), 147.07 (1C, C$_{60}$), 147.16 (2C, C$_{60}$), 147.24 (2C, C$_{60}$), 148.20 (2C, C$_{60}$), 148.39 (1C, C$_{60}$), 156.49 (2C, C$_{60}$), 159.93 (2C, C$_{60}$);

APCI-HRMS (−): calcd for C$_{66}$H$_{15}$OSi (M−H$^+$), 851.08922; found, 851.08765.

Example 9

Production of C$_{60}$(CH$_3$)H

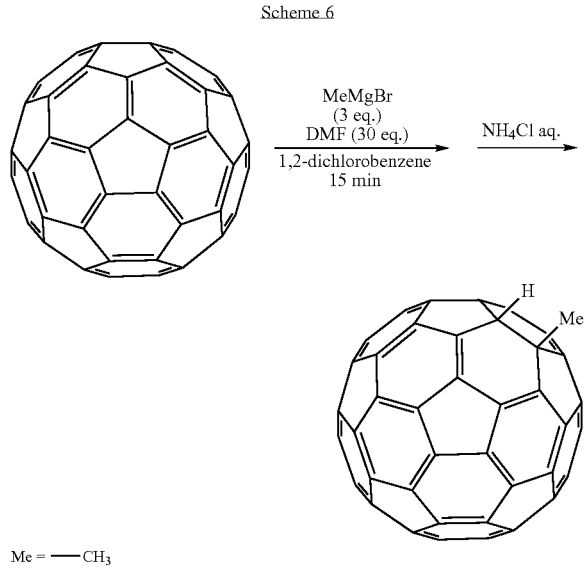

Scheme 6

Me = ——CH$_3$

C$_{60}$(CH$_3$)H was synthesized in a manner similar to that in Example 1 except that: 40.0 mg of C$_{60}$, 10 mL of 1,2-dichlorobenzene and 0.129 mL of DMF were used; and MeMgBr (0.167 mL, 1.0 M, 0.167 mmol) was used instead of Me$_3$SiCH$_2$MgCl (18.7 mg, isolated yield: 46%).

Regarding the obtained C$_{60}$(CH$_3$)H, the measurement of APCI-HRMS utilizing $^1$H NMR, $^{13}$C NMR and TOF method was carried out. Results are shown below:

$^1$H NMR (500 MHz, CDCl$_3$/CS$_2$): δ 3.26 (s, 3H, CH$_3$), 6.40 (s, 1H, C$_{60}$H);

$^{13}$C NMR (125 MHz, CDCl$_3$/CS$_2$): δ 35.05 (1C, CH$_3$), 60.12 (1C, C$_{60}$CH$_3$), 61.30 (1C, C$_{60}$H), 135.20 (2C, C$_{60}$), 136.33 (2C, C$_{60}$), 140.07 (2C, C$_{60}$), 140.32 (2C, C$_{60}$), 141.55 (2C, C$_{60}$), 141.56 (2C, C$_{60}$), 141.85 (2C, C$_{60}$), 141.90 (2C, C$_{60}$), 141.92 (2C, C$_{60}$), 142.06 (2C, C$_{60}$), 142.44 (2C+2C, C$_{60}$), 143.14 (2C, C$_{60}$), 144.51 (2C, C$_{60}$), 144.57 (2C, C$_{60}$), 145.26 (2C, C$_{60}$), 145.27 (2C, C$_{60}$), 145.33 (2C, C$_{60}$), 145.39 (2C, C$_{60}$), 145.71 (2C, C$_{60}$), 145.77 (2C, C$_{60}$), 146.06 (2C, C$_{60}$), 146.11 (2C, C$_{60}$), 146.22 (2C, C$_{60}$), 146.29 (2C, C$_{60}$), 146.82 (2C, C$_{60}$), 147.20 (1C, C$_{60}$), 147.32 (1C, C$_{60}$), 153.46 (2C, C$_{60}$), 156.84 (2C, C$_{60}$);

APCI-HRMS (−): calcd for C$_{61}$H$_3$ (M−H$^+$), 735.02348; found, 735.02325.

Example 10

Production of C$_{60}$(C$_6$H$_4$OCH$_3$)H

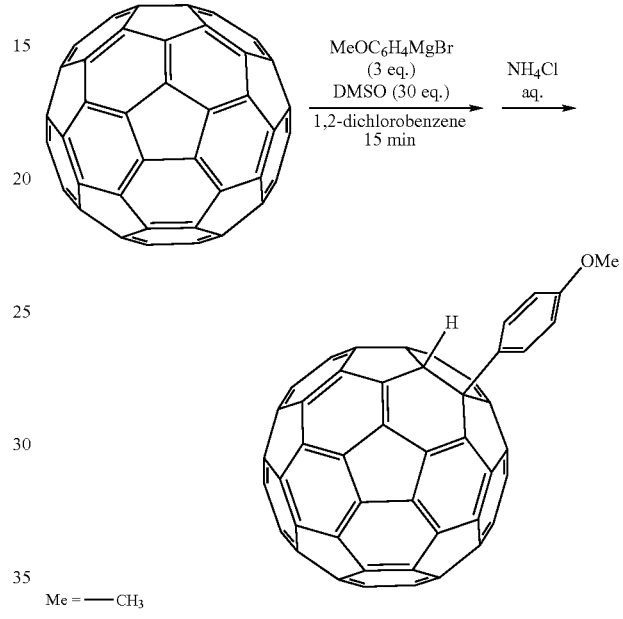

Scheme 7

Me = ——CH$_3$

Synthesis was carried out in a manner similar to that in Example 1 except that: 40.0 mg of C$_{60}$ and 10 mL of 1,2-dichlorobenzene were used; MeOC$_6$H$_4$MgBr (0.211 mL, 0.790 M, 0.167 mmol) was used instead of Me$_3$SiCH$_2$MgCl; and dimethyl sulfoxide (DMSO) (118 μL, 1.67 mmol) was used instead of DMF. Purification was carried out using silica gel column chromatography (eluting solution: carbon disulfide/hexane=2/1) to obtain C$_{60}$(C$_6$H$_4$OCH$_3$)H (24.5 mg, isolated yield: 53%)

Regarding the obtained fullerene derivative C$_{60}$(C$_6$H$_4$OCH$_3$)H, the measurement of APCI-HRMS utilizing $^1$H NMR, $^{13}$C NMR and TOF method was carried out. Results are shown below:

$^1$H NMR (400 MHz, CDCl$_3$/CS$_2$): δ 3.97 (s, 3H, CH$_3$), 6.71 (s, 1H, C$_{60}$H), 7.26 (m, 2H, C$_6$H$_4$), 8.34 (m, 2H, C$_6$H$_4$);

$^{13}$C NMR (100 MHz, CDCl$_3$/CS$_2$): δ 55.21 (1C, CH$_3$), 63.77 (1C, C$_{60}$H), 67.21 (1C, C$_{60}$C), 115.13 (2C, C$_6$H$_4$), 128.62 (2C, C$_6$H$_4$), 135.59 (2C, C$_{60}$), 136.21 (2C, C$_{60}$), 140.13 (2C, C$_{60}$), 140.20 (2C, C$_{60}$), 140.40 (1C, C$_6$H$_4$), 141.48 (2C, C$_{60}$), 141.55 (2C, C$_{60}$), 141.86 (2C, C$_{60}$), 141.92 (2C, C$_{60}$), 141.94 (2C, C$_{60}$), 142.21 (2C, C$_{60}$), 142.46 (2C, C$_{60}$), 142.47 (2C, C$_{60}$), 143.17 (2C, C$_{60}$), 144.46 (2C, C$_{60}$), 144.55 (2C, C$_{60}$), 145.28 (2C, C$_{60}$), 145.31 (2C, C$_{60}$), 145.39 (2C, C$_{60}$), 145.42 (2C, C$_{60}$), 145.71 (2C, C$_{60}$), 145.82 (2C, C$_{60}$), 146.08 (2C, C$_{60}$), 146.10 (2C, C$_{60}$), 146.25 (2C, C$_{60}$), 146.30 (2C, C$_{60}$), 146.75 (2C, C$_{60}$), 147.17 (1C, C$_{60}$), 147.40 (1C, C$_{60}$), 152.53 (2C, C$_{60}$), 154.02 (2C, C$_{60}$), 159.20 (1C, C$_6$H$_4$);

APCI-HRMS (−): calcd for C$_{67}$H$_7$O (M−H$^+$), 827.05096; found, 827.04969.

INDUSTRIAL APPLICABILITY

The present invention can be utilized, for example, for an electron-conductive material, a semiconductor material, an optical functional material.

The invention claimed is:

1. A method for producing a fullerene derivative which is a mono(organo)fullerene derivative, a di(organo)fullerene derivative, a tri(organo)fullerene derivative or a tetra(organo)fullerene derivative comprising the organic group addition step A for adding an organic group by reacting at least a Grignard reagent and a polar substance with a fullerene or fullerene derivative, in which the polar substance having the donor number of 25 to 33.1 is used in an amount of 3 to 100 equivalents of the fullerene or fullerene derivative to which the organic group is added; wherein the polar substance is not pyridine.

2. The method for producing a fullerene derivative according to claim 1, in which the fullerene or fullerene derivative to which the organic group is added in the organic group addition step A is a fullerene or fullerene derivative represented by the following formula (1):

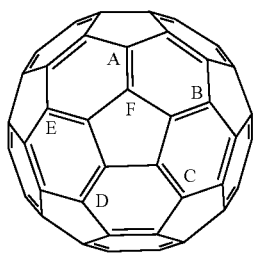

(1)

wherein: organic groups have been each independently added to 0 to 4 carbons among 5 carbons positioned at A to E; and a hydrogen atom or $C_1$-$C_{30}$ hydrocarbon group has been added to a carbon positioned at F, or nothing has been added thereto.

3. The method for producing a fullerene derivative according to claim 2, wherein in the organic group addition step A, the organic group is added to at least one of the carbons positioned at A to E in the fullerene or fullerene derivative represented by formula (1) to which the organic group has not been added.

4. The method for producing a fullerene derivative according to claim 1, wherein the organic group for addition in the organic group addition step A is one or more substances selected from the group consisting of a hydrogen atom, a substituted or unsubstituted $C_1$-$C_{30}$ hydrocarbon group, a substituted or unsubstituted $C_1$-$C_{30}$ alkoxy group, a substituted or unsubstituted $C_6$-$C_{30}$ aryloxy group, a substituted or unsubstituted amino group, a substituted or unsubstituted silyl group, a substituted or unsubstituted alkylthio group (—$SY^1$: in the formula, $Y^1$ is a substituted or unsubstituted $C_1$-$C_{20}$ alkyl group), a substituted or unsubstituted arylthio group (—$SY^2$: in the formula, $Y^2$ is a substituted or unsubstituted $C_6$-$C_{18}$ aryl group), a substituted or unsubstituted alkylsulfonyl group (—$SO_2Y^3$: in the formula, $Y^3$ is a substituted or unsubstituted $C_1$-$C_{20}$ alkyl group), or a substituted or unsubstituted arylsulfonyl group (—$SO_2Y^4$: in the formula, $Y^4$ is a substituted or unsubstituted $C_6$-$C_{18}$ aryl group).

5. The method for producing a fullerene derivative according to claim 1, wherein the organic group for addition in the organic group addition step A is a group represented by the following formula (2):

(2)

wherein $R^{21}$ to $R^{23}$ are each independently a hydrogen atom, a substituted or unsubstituted $C_1$-$C_{30}$ hydrocarbon group, a substituted or unsubstituted $C_1$-$C_{30}$ alkoxy group, a substituted or unsubstituted $C_6$-$C_{30}$ aryloxy group, a substituted or unsubstituted amino group, a substituted or unsubstituted silyl group, a substituted or unsubstituted alkylthio group (—$SY^1$: in the formula, $Y^1$ is a substituted or unsubstituted $C_1$-$C_{20}$ alkyl group), a substituted or unsubstituted arylthio group (—$SY^2$: in the formula, $Y^2$ is a substituted or unsubstituted $C_6$-$C_{18}$ aryl group), a substituted or unsubstituted alkylsulfonyl group (—$SO_2Y^3$: in the formula, $Y^3$ is a substituted or unsubstituted $C_1$-$C_{20}$ alkyl group), or a substituted or unsubstituted arylsulfonyl group (—$SO_2Y^4$: in the formula, $Y^4$ is a substituted or unsubstituted $C_6$-$C_{18}$ aryl group).

6. The method for producing a fullerene derivative according to claim 5, wherein $R^{21}$ to $R^{23}$ are each independently a $C_1$-$C_{20}$ alkyl group.

7. The method for producing a fullerene derivative according to claim 1, wherein the Grignard reagent is represented by the following formula (3):

$R^3MgX$ (3)

wherein: $R^3$ represents an organic group; and X represents Cl, Br or I.

8. The method for producing a fullerene derivative according to claim 7, wherein $R^3$ in formula (3) is a substituted or unsubstituted $C_1$-$C_{30}$ hydrocarbon group, a substituted or unsubstituted $C_1$-$C_{30}$ alkoxy group, a substituted or unsubstituted $C_6$-$C_{30}$ aryloxy group, a substituted or unsubstituted amino group, a substituted or unsubstituted silyl group, a substituted or unsubstituted alkylthio group (—$SY^1$: in the formula, $Y^1$ is a substituted or unsubstituted $C_1$-$C_{20}$ alkyl group), a substituted or unsubstituted arylthio group (—$SY^2$: in the formula, $Y^2$ is a substituted or unsubstituted $C_6$-$C_{18}$ aryl group), a substituted or unsubstituted alkylsulfonyl group (—$SO_2Y^3$: in the formula, $Y^3$ is a substituted or unsubstituted $C_1$-$C_{20}$ alkyl group), or a substituted or unsubstituted arylsulfonyl group (—$SO_2Y^4$: in the formula, $Y^4$ is a substituted or unsubstituted $C_6$-$C_{18}$ aryl group).

9. The method for producing a fullerene derivative according to claim 8, wherein $R^3$ is a $C_1$-$C_{20}$ alkyl group.

10. The method for producing a fullerene derivative according to claim 1, wherein the Grignard reagent is used in an amount of 1 to 20 equivalents of the fullerene or fullerene derivative to which the organic group is added in the organic group addition step A.

11. The method for producing a fullerene derivative according to claim 1, wherein the donor number of the polar substance is 26.6 to 33.1.

12. The method for producing a fullerene derivative according to claim 1, wherein the polar substance is N,N-dimethylformamide or dimethyl sulfoxide.

13. The method for producing a fullerene derivative according to claim 1, wherein the fullerene derivative to which the organic group has been added in the organic group addition step A is a fullerene derivative represented by the following formula (1A):

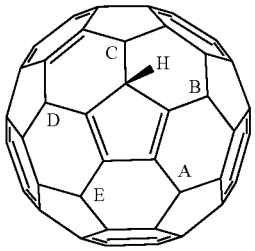

(1A)

wherein: organic groups have been each independently added to 1 to 5 carbons among 5 carbons positioned at A to E.

14. The method for producing a fullerene derivative according to claim 13, wherein in formula (1A), the organic groups added to the carbons positioned at A to E are each independently a hydrogen atom, a substituted or unsubstituted $C_1$-$C_{30}$ hydrocarbon group, a substituted or unsubstituted $C_1$-$C_{30}$ alkoxy group, a substituted or unsubstituted $C_6$-$C_{30}$ aryloxy group, a substituted or unsubstituted amino group, a substituted or unsubstituted silyl group, a substituted or unsubstituted alkylthio group (—$SY^1$: in the formula, $Y^1$ is a substituted or unsubstituted $C_1$-$C_{20}$ alkyl group), a substituted or unsubstituted arylthio group (—$SY^2$: in the formula, $Y^2$ is a substituted or unsubstituted $C_6$-$C_{18}$ aryl group), a substituted or unsubstituted alkylsulfonyl group (—$SO_2Y^3$: in the formula, $Y^3$ is a substituted or unsubstituted $C_1$-$C_{20}$ alkyl group), or a substituted or unsubstituted arylsulfonyl group (—$SO_2Y^4$: in the formula, $Y^4$ is a substituted or unsubstituted $C_6$-$C_{18}$ aryl group).

15. The method for producing a fullerene derivative according to claim 1, which comprises the organic group addition step B for further adding an organic group by reacting at least a basic compound and a halogen compound with the fullerene derivative obtained by addition of a hydrogen atom and an organic group in the organic group addition step A.

16. The method for producing a fullerene derivative according to claim 15, wherein the basic compound to be used in the organic group addition step B comprises one or more substances selected from the group consisting of a metal hydride, a metal alkoxide, an alkali metal reagent, an alkali metal and an organic alkali.

17. The method for producing a fullerene derivative according to claim 15, wherein the basic compound to be used in the organic group addition step B is alkoxide comprising K or Na.

18. The method for producing a fullerene derivative according to claim 15, wherein the basic compound to be used in the organic group addition step B is t-BuOK or t-BuONa.

19. The method for producing a fullerene derivative according to claim 15, wherein the halogen compound to be used in the organic group addition step B is represented by the following formula (4):

$$R^4X \qquad (4)$$

wherein: $R^4$ represents an organic group; and X represents a halogen atom.

20. The method for producing a fullerene derivative according to claim 19, wherein in formula (4): $R^4$ is a hydrogen atom, a substituted or unsubstituted $C_1$-$C_{30}$ hydrocarbon group, a substituted or unsubstituted $C_1$-$C_{30}$ alkoxy group, a substituted or unsubstituted $C_6$-$C_{30}$ aryloxy group, a substituted or unsubstituted amino group, a substituted or unsubstituted silyl group, a substituted or unsubstituted alkylthio group (—$SY^1$: in the formula, $Y^1$ is a substituted or unsubstituted $C_1$-$C_{20}$ alkyl group), a substituted or unsubstituted arylthio group (—$SY^2$: in the formula, $Y^2$ is a substituted or unsubstituted $C_6$-$C_{18}$ aryl group), a substituted or unsubstituted alkylsulfonyl group (—$SO_2Y^3$: in the formula, $Y^3$ is a substituted or unsubstituted $C_1$-$C_{20}$ alkyl group), or a substituted or unsubstituted arylsulfonyl group (—$SO_2Y^4$: in the formula, $Y^4$ is a substituted or unsubstituted $C_6$-$C_{18}$ aryl group); and X is Cl, Br or I.

21. The method for producing a fullerene derivative according to claim 1, wherein in the organic group addition step A, the organic group is added to one of the carbons in the fullerene or fullerene derivative, to which the organic group has not been added.

* * * * *